United States Patent [19]

Radna

[11] Patent Number: 5,402,773
[45] Date of Patent: Apr. 4, 1995

[54] AUXILIARY SURGICAL RETRACTOR SYSTEM

[76] Inventor: Richard J. Radna, 1165 Park Ave., New York, N.Y. 10128

[21] Appl. No.: 118,642

[22] Filed: Sep. 10, 1993

[51] Int. Cl.6 .......................................... A61B 17/02
[52] U.S. Cl. ..................... 128/20; 446/111; 446/120
[58] Field of Search .............. 128/20, 17, 3; 446/111, 446/112, 120; 606/191, 198

[56] References Cited

U.S. PATENT DOCUMENTS

| | | | |
|---|---|---|---|
| 2,473,266 | 6/1949 | Wexler | 128/20 |
| 3,522,799 | 8/1970 | Gauthier | 128/20 |
| 3,566,531 | 3/1971 | Hasel et al. | 446/120 |
| 3,570,475 | 3/1971 | Weinstein | 128/20 |
| 4,606,732 | 8/1986 | Lyman | 446/120 |
| 4,616,635 | 10/1986 | Caspar et al. | 128/20 |
| 4,817,587 | 4/1989 | Janese | 128/20 |
| 5,271,384 | 12/1993 | McEwen et al. | 128/20 |
| 5,280,782 | 1/1994 | Wilk | 128/20 |

FOREIGN PATENT DOCUMENTS

| | | | |
|---|---|---|---|
| 1015366 | 9/1957 | Denmark | 446/111 |
| 455282 | 11/1991 | European Pat. Off. | 606/198 |
| 773318 | 11/1934 | France | 446/111 |
| 2662929 | 12/1991 | France | 128/20 |

*Primary Examiner*—Richard J. Apley
*Assistant Examiner*—Donna L. Maraglio
*Attorney, Agent, or Firm*—Sherman and Shalloway

[57] ABSTRACT

The present invention describes an auxiliary surgical retractor blade system in which a plurality of blade members are connectable in series by connector elements. The connector elements engage receivers on adjacent blade members and the receivers themselves are formed with flat abutting wall surfaces to prevent relative movement of the adjacent blade sections. Retention means may be provided in conjunction with the connector elements and receivers to prevent inadvertent disconnection of adjacent blade sections. The auxiliary retractor blade system of the present invention is useable with existing surgical retraction instruments to extend their reach along the length of a surgical incision.

15 Claims, 4 Drawing Sheets

AUXILIARY SURGICAL RETRACTOR SYSTEM

BACKGROUND OF THE INVENTION

Retractors are used in surgery to keep the tissues on either side of an incision apart thereby opening the surgical site. In addition, they are used to move intervening organs out of the way and to hold them so the surgeon has a clear view of the surgical site. However, retraction is limited by the length and width of the blade of the retraction instrument. In some cases, multiple retractors are necessary to maintain a long incision; this is particularly true in the case of spinal surgery. The presence of multiple retractors along the length of the incision can present problems such as entanglement of other instruments or tissues in the mechanisms of those retractors, or they can simply get in the way of the surgeon.

A variety of retractors have been developed in attempts to provide both better retraction and to alleviate some of the other problems encountered. For example, U.S. Pat. No. 2,473,266, Wexler discloses a self retaining abdominal retractor in which a frame surrounds the surgical site and provides means for attaching retractor blades to it. However, this frame is limited in its size and remains above and surrounding the surgical site where other instruments or materials may get caught on it. U.S. Pat. No. 5,052,373, Michelson, discloses a spinal retractor which includes a frame comprising a pair of spreadable arms on which pairs of blade sets are self engaging. Although this device is adjustable, its reach is limited by the length of the arms.

The present invention overcomes the problems and limitations of the prior art by providing an auxiliary surgical retractor blade system which is extremely variable in length and which can be used with most types of prior retraction instruments, including that of Michelson, to provide a free floating buttress which is pressed against the tissues of the surgical wound by a minimum of conventional retractor instruments. The system also provides for variability in blade height making it useful for deep incisions.

SUMMARY OF THE INVENTION

It is an object of this invention to provide an auxiliary surgical retractor system.

It is a further object to provide an auxiliary surgical retractor system which is readily adjustable in length yet provides a substantially rigid retractor blade.

It is a still further object to provide an auxiliary surgical retractor system wherein individual blade sections are serially connected and may be connected at angles corresponding to particular anatomical angles.

It is an even further object to provide an auxiliary surgical retractor system which can be used with most other types of retraction instruments to extend the reach of those instruments.

Further objects and advantages will be apparent from the following drawings and description.

The present invention is directed to an auxiliary surgical retractor blade system which provides the surgeon with a readily adjustable means for tissue retraction and which can be used in conjunction with most types of existing retraction instruments. The system comprises a plurality of blade members and connector elements whereby the blade members are connectable in series by the connector elements to form auxiliary surgical retractor blades of variable lengths and heights. The blade members comprise a blade body with receiving means for the connector elements on each end of the blade body. The connector elements comprise pins having at least two legs which fit into the correspondingly shaped receiving means on adjacent blade sections, the legs of the pins being rigidly connected to thereby link the blade members together. The connector elements are provided in varying sizes and forms which permit the blade members to be connected in a linear and/or a vertically stacked arrangement as well as at angles which correspond to anatomical angles of a patient. Thus, by adding or removing sections, the blade system of this invention may be tailored to fit the particular surgical circumstances. In addition, the retractor blade system of the present invention has sufficient rigidity so that it may be used with most types of retraction instruments as a buttress against the tissues of the surgical site along an extended length of an incision with the retractive force being provided by one or two instruments at the ends of the serially joined sections. In this manner, the rigid frames surrounding the surgical site that other types of retractors use are not necessary thus keeping the site clear of potential entanglements. In addition, the auxiliary retractor system of the present invention provides an extended reach along an incision beyond that of conventional retractors.

DETAILED DESCRIPTION OF THE INVENTION

Figure 1:
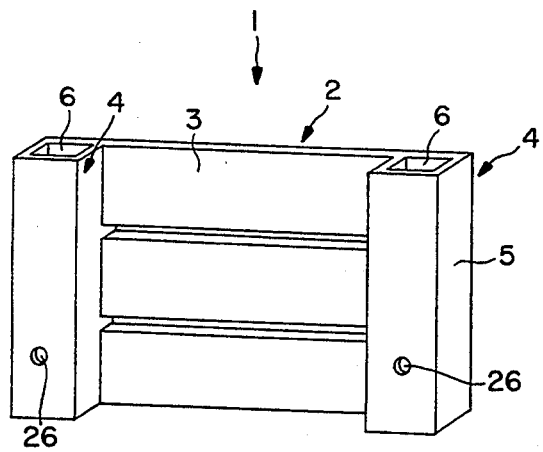
FIG. 1 is an oblique view of a first embodiment of a retractor blade section according to the present invention.

The present invention is directed to an auxiliary surgical retractor blade system which comprises a plurality of blade members and a means to connect them in a serial manner to construct a substantially rigid retractor blade of variable length and height. The drawing figures illustrate alternative embodiments of the blade sections and the connectors, however, there are features which are common to all embodiments.

Figure 7:
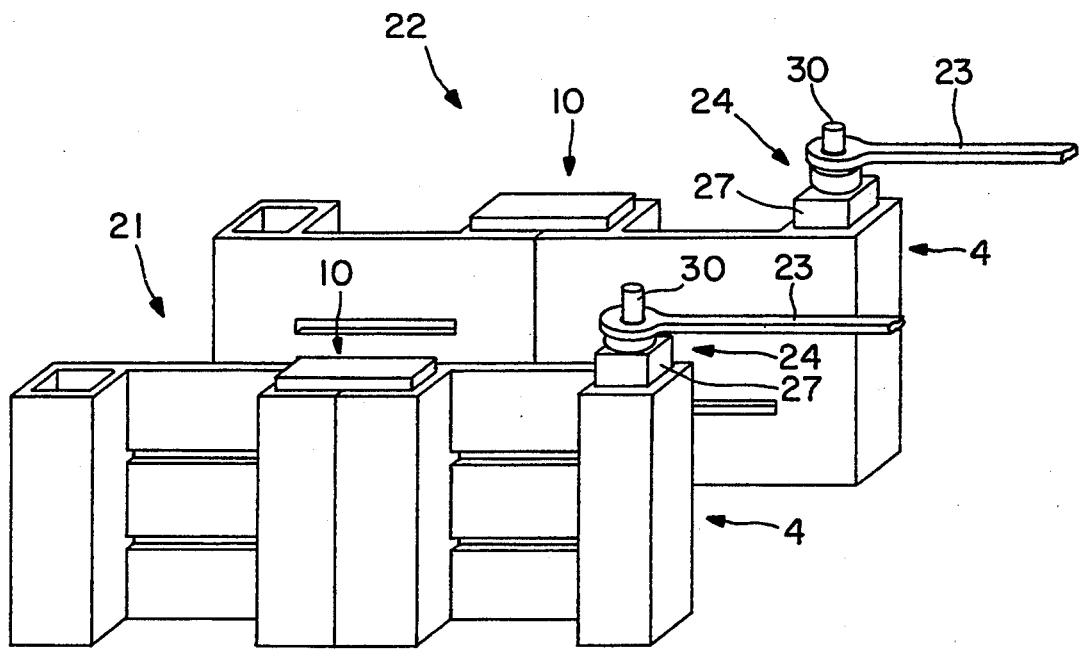
FIG. 7 is an oblique view illustrating assembled auxiliary retractor blades of the present invention arranged for use and with the arms of a retractor handle attached.

In the embodiment of FIG. 1, blade member 1 comprises blade portion 2 which is illustrated as being formed of a plurality of parallel slats 3. Along opposite edges of blade portion 2 are elongated connector sleeves 4 into which legs 13, 15 of connector elements 10, 11 and 14 shown in FIGS. 3, 4, 10 and 11 are inserted to serially connect two blade members 1 together as shown in FIG. 5. Although illustrated as having a preferably rectangular cross section, connector sleeves 4 may be formed with any polygonal cross section. Preferably, however, the endmost outer surface 5 of each connector sleeve 4 should be flat and perpendicular to the plane of blade portion 2 so as to abut the corresponding sleeve of the next adjacent blade member 1 as shown in FIG. 5 thereby providing rigidity to the assembly. Centrally disposed through the length of connector sleeves 4 is a longitudinal channel 6 which preferably has the same shape cross section as connector sleeves 4. Longitudinal channel 6 preferably extends the full length of connector sleeves 4 which themselves are of a sufficient length so as to provide rigidity to an assemblage of blade sections 1. Preferably, connector sleeves 4 at each end of blade portion 2 extend the full height of blade member 1 and are located on the same side of blade portion 2 as illustrated in the figures. In use, the side of blade member 1 on which connector sleeves 4 are located is the side which contacts and presses against the tissues being retracted. In this manner, the opposite side of blade members 1 presents a relatively smooth and even surface, as seen in FIG. 7, which bounds the surgical field within the incision.

Figure 2:
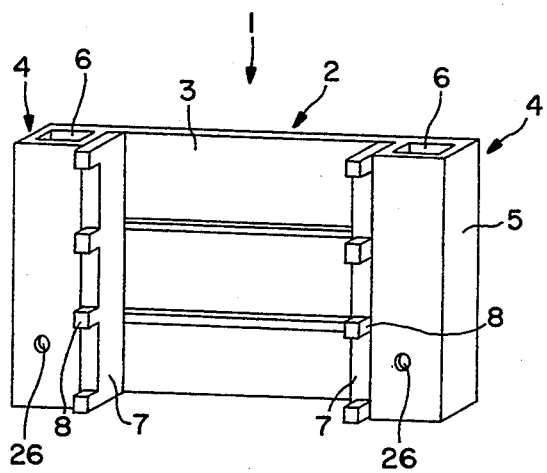
FIG. 2 is an oblique view of a second embodiment of a retractor blade section according to the present invention.
Figure 8:
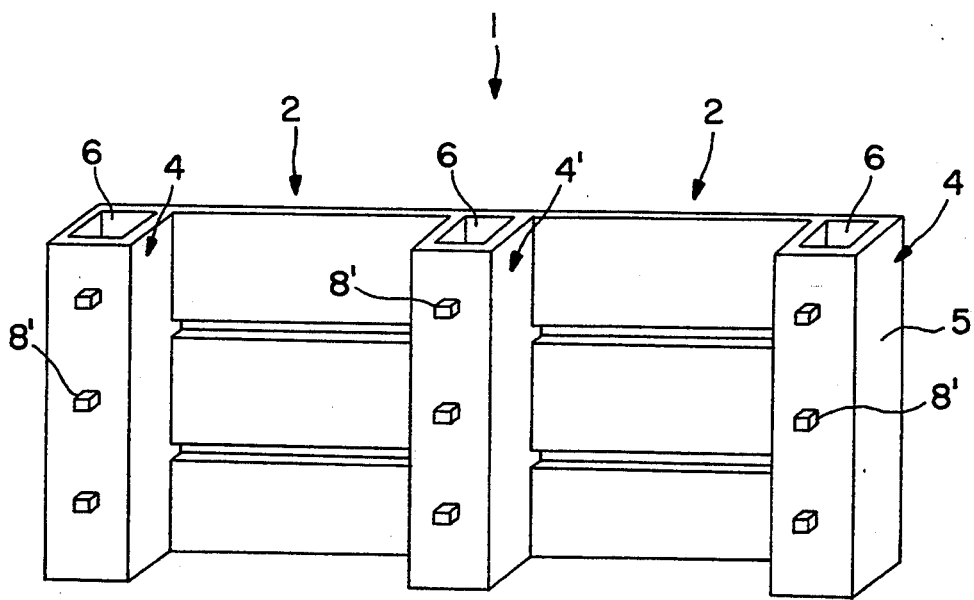
FIG. 8 is an oblique view of a third embodiment of a retractor blade section according to the present invention.

FIG. 2 illustrates an alternative embodiment of blade member 1 wherein tooth plates 7 are provided on blade members 1. Tooth plates 7 have teeth or hooks 8 which extend beyond connector sleeves 4 on the side of blade member 1 opposite to blade portion 2 to contact the tissues surrounding a surgical incision where the blade sections are in use. Teeth 8 provide a means whereby slippage of blade members 1 against the tissues is reduced. Teeth 8 may have any suitable shape but are preferably of a design to maximize blade stability against the tissues while minimizing tissue trauma. Teeth 8 shown in FIG. 2 have a substantially rectangular or block-like shape, whereas in the alternative emobodiment of FIG. 8, teeth 8' have rounded ends. Other shapes, including but not limited to conical, pyramidal, or hook shaped teeth may also be used. In the embodiment of FIG. 2, tooth plates 7 may be fabricated separately from blade member 1 and either fixedly or removably attached to connector sleeves 4. Alternatively, plates 7 and teeth 8 may be molded or cast as an integral part of connector sleeves 4 or connector sleeves 4 may be modified to have teeth 8' molded or cast as an integral part of the tissue contacting face thereof as shown in FIG. 8. The embodiment of FIG. 8 also illustrates an extra connector sleeve 4' being located midway between connector sleeves 4 at each end of blade member 1.

Blade portions 2 are illustrated as comprising three parallel slats; however, they may have fewer or more slats and still be within the scope of this invention. Additionally, blade portions 2 may also be solid plates. Thus, blade portions 2 may be given virtually any form, what is important to this invention is that they have, at opposite edges, means to permit their serial connection to form an extended length assembly from a plurality of blade members 1.

Figure 3:
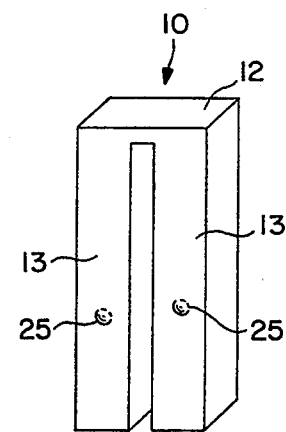
FIG. 3 is an oblique view of a first embodiment of a connector element according to the present invention.
Figure 4:
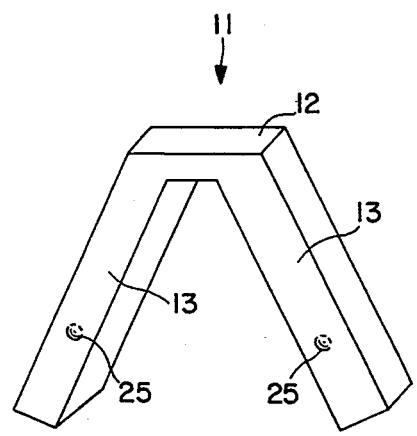
FIG. 4 is an oblique view of a second embodiment of a connector element according to the present invention.
Figure 5:
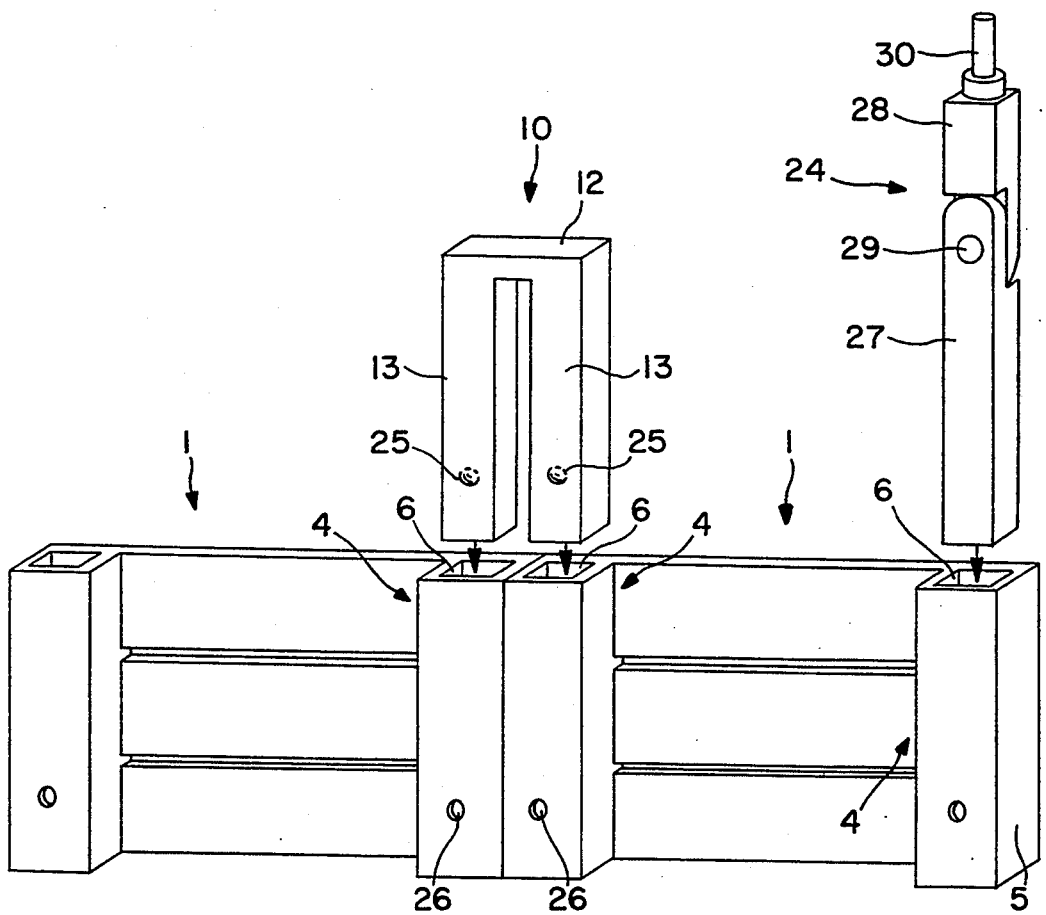
FIG. 5 is an oblique view showing the connection of two blade sections of the first, embodiment with a connector of the first embodiment.

Turning now to FIGS. 3 and 4, first and second connector elements 10 and 11 are illustrated. Each connector element 10 and 11 comprises a head 12 from which depend two legs 13. In first connector element 10 of FIG. 3, legs 13 are parallel and spaced apart a distance equivalent to the thickness of abutting walls of connector sleeves 4. This is more clearly shown in FIG. 5 where connector element 10 is positioned for insertion into connector sleeves 4 of adjacent blade members 1. FIG. 5 also illustrates the importance of the flat outermost surface 5 of connector sleeves 4 as it permits blade members 1 to firmly abut each other and serves to increase the rigidity of the assembly by providing a block at the point of connection of two blade members 1.

Figure 6:
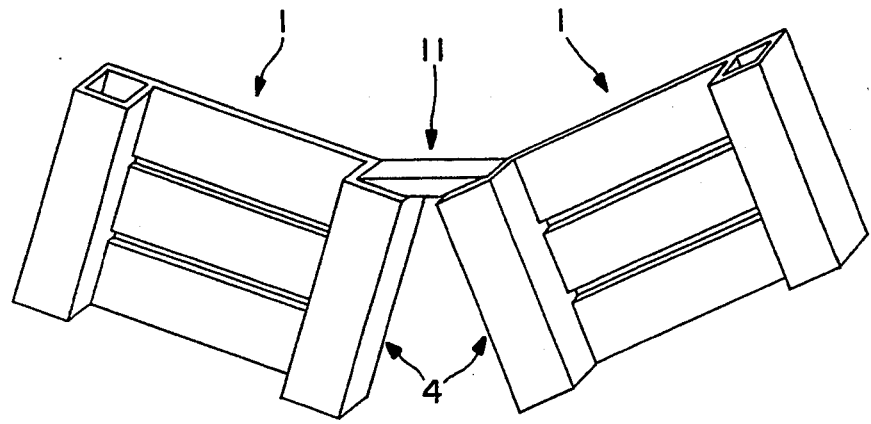
FIG. 6 is an oblique view showing the connection of two blade sections with a connector of the second embodiment.

Second connector element 11 depicted in FIG. 4 provides legs 13 at a fixed angle so that legs 13 diverge from head 12. This form allows blade members 1 to be connected at angles which will accommodate differing anatomical angles such as the interface between the lumbar spine and the sacrum or between the cervical spine and the head of a patient. Such an angular connection of blade members 1 is illustrated in FIG. 6. Although second connector element 11 may be provided with legs 13 fixed at any angle, the most commonly preferred angles are 15°, 30°, 60° and 90°.

Figure 9:
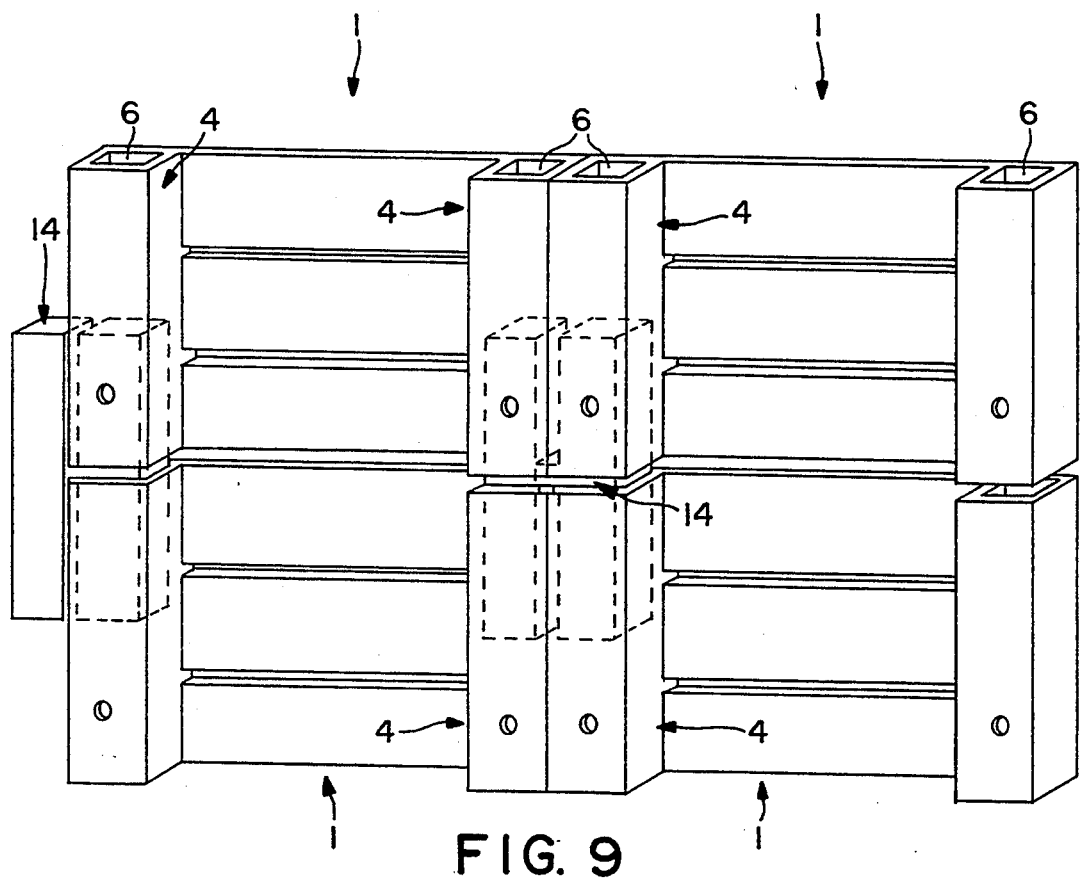
FIG. 9 is an oblique view showing four blade sections of the present invention assembled in a serial and stacked arrangement.
Figure 10:
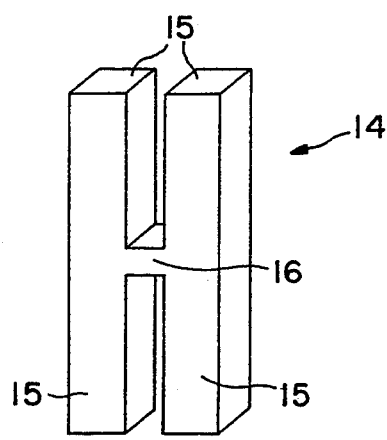
FIG. 10 is an oblique view of a third embodiment of a connector element according to the present invention.
Figure 11:
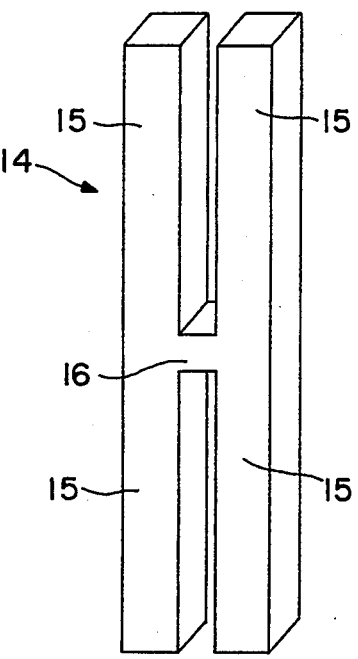
FIG. 11 is an alternative form of the connector of FIG. 10.

The auxiliary retractor system of this invention is not restricted to use in a horizontal manner along an incision. Where the surgical site is deep, blade members 1 may be connected in multiple rows and used vertically through the depth of a surgical wound in the manner shown in FIG. 9. As illustrated therein, blade members 1, in addition to being connected horizontally, may be stacked vertically through the use of a third connector element 14 having an "H" shape. First and second alternative forms of third connector 14 are illustrated in FIGS. 10 and 11. Third connector 14 comprises upper and lower pairs of legs 15 with a cross bar 16 at the mid-point. As with first connector element 10, legs 15 of third connector 14 are parallel and spaced apart a distance equivalent to the thickness of the abutting walls of connector sleeves 4 of adjacent blade members 1.

The two forms of third connector 14 are best described as short, FIG. 10, and long, FIG. 11. In the short form, upper and lower pairs of legs 15 are each about one half the length of connector sleeves 4 of blade members 1. This relationship is more clearly shown in FIG. 9 where third connector 14 is shown connecting four blade members 1 in a horizontally linear and vertically stacked arrangement to form a double height auxiliary retractor blade for use in deep incisions. The short form of third connector 14 leaves half the length of channels 6 open for engagement by further connectors 10, 11 or 14 or by an engaging means of a retractor handle. The long form of third connector 14 is used in circumstances when it is not necessary to maintain access to a portion of the channels 6 in connector sleeves 4. Although ordinarily provided with legs having a length equivalent to that of connector sleeves 4, for use in combination with the short form of third connector 14, first and second connectors 10 and 11 may be provided with legs 13 which are about one half the length of connector sleeves 4.

Each embodiment of the present invention may also include retention means in combination with connector sleeves 4 and connector elements 10, 11 and 14 which cooperate to ensure that connected blade members 1 do not inadvertently separate during use. The drawing figures illustrate one form of such retention means as cooperating ball 25 and hole 26 detents. Preferably, balls 25 are provided on legs 13, 15 of connector elements 10, 11 and 14. Cooperating holes 26 are formed in connector sleeves 4. Alternatively, the legs 13, 15 of connector elements 10, 11 and 14 may be slightly sprung so as to be biased against the inside surfaces of longitudinal channels 6 of sleeves 4 when inserted therein. Also alternatively, a latch mechanism may be provided on sleeves 4 which extends through the sleeve wall to engage connector legs 13, 15 inserted therein. Other retention means adaptable to this construction may also be used.

As noted previously, the auxiliary retractor blade system of this invention may be used with the handle portion of most types of surgical retraction instruments and as an adjunct to the existing blades of such instruments. Such retraction instruments include, but are not limited to, Cloward type retractors, Gelpi type retractors and Scoville type retractors. FIG. 7 illustrates one manner of such use wherein two auxiliary blades 21 and 22 made up of two blade members 1 each connected by means of connector element 10 of FIG. 3 are shown with arms 23 of a Cloward type retractor handle connected to blades 21 and 22. The Cloward type retractor handle is well known and has a reverse scissor handle whereby operation of the retractor handle causes arms 23 to spread apart. In this manner of use arms 23 engage junction connectors 24 placed in connector sleeves 4 of auxiliary blades 21 and 22. Manipulation of the retrator handle to open arms 23 causes auxiliary blades 21 and 22 to separate and to thereby press against and retract the tissues around the surgical site. By locking the retractor handle, retraction of the tissues continues until the handle is released. For short incisions, the rigidity of blade sections 1 allows sufficient retraction to be achieved with one retractor handle connected at one end of auxiliary blades 21 and 22. For longer incisions, such as in major spinal surgery, a retractor handle at each end of auxiliary blades 21 and 22 is preferably used. The rigidity of blades 21 and 22 allows them to act like a buttress against the tissues to provide retraction along the length of the incision. In this manner a minimum of retractor handles is required and the surgical site is substantially unobstructed by the retraction means.

Junction connectors 24 may take any form necessary to engage the retraction instrument. However, they will at least have a body portion 27 of a size and shape to fit in channels 6 of the connector sleeves 4. FIG. 5 illustrates one form of a junction connector 24 which includes an upper connecting portion 28 which is pivotally joined to body portion 27 by pin 29. Upper connecting portion 28 includes a pin 30 or other means whereby a retractor handle can engage junction connector 24, such as is shown in FIG. 7. The pivotal joint between upper connecting portion 28 and body portion 27 allows the surgeon a certain degree of flexibility in placing the retractor handles in relation to the auxiliary blades and the patient. Alternatively, junction connector 24 may be a simple body 27 and engagement means 30 which fits into connector sleeve 4 as shown in FIG. 7. As with connector elements 10, 11 and 14, body 27 of junction connector 24 may be provided in lengths corresponding to the full length of connector sleeves 4 or to one half that length.

Although the Cloward type of retractor handle has been mentioned as being used in connection with this invention, other types of retraction instruments may also be used including the Michelson device discussed previously as well as instruments which may have integral retractor blades. With such instruments, the auxiliary blades of this invention form a wall or fence against which the existing blades of the retraction instrument are placed. Retraction force is then applied and the auxiliary blades again act as a buttress to spread the retraction along the length of the incision. The effect of the use of the auxiliary blades of the present invention is to provide even pressure on the tissues being retracted and to provide unobstructed access to the surgical wound. The even retractor pressure obtained with this invention results in diminished ischemic changes to the muscles and other tissues being retracted.

Returning to the blade member embodiment of FIG. 8, it is readily seen that the mid-position connector sleeve 4' of this embodiment provides an additional location for insertion of a junction connector 24 as well as for connection to other blade members 1. Blade members 1 of this invention may be provided in various sizes although the preferred sizes are 1½, 2 and 3 inches in length, with an approximate height of 1 to 1½ inches. Longer blade members may also be fabricated and may have more than one mid-position connector sleeve 4' along their lengths. By providing the longer sizes of blade members 1 with the mid-position connector sleeves 4', a variety of combinations may be assembled using the different connector elements 10, 11 and 14 and the different sizes of blade members 1 thereby allowing the surgeon to tailor the auxiliary blade to the particular surgical circumstances.

Blade members 1 and connector elements 10, 11 and 14 of this invention may be made of any material having the necessary rigidity, strength, resiliency and ability to withstand surgical sterilization procedures. The preferred material is, of course, surgical stainless steel. However, other suitable metals or reinforced polymers may also be used. In addition, the parts may be manufactured by any appropriate means including machining, casting or molding.

The present invention, although useful in any type of surgery, has particular utility in spinal surgery where a wide, unobstructed surgical field is desired and where uniform support of the surrounding tissues is required. The modular nature of the blade members allows expansion both lengthwise and depthwise to accommodate virtually any size and location of surgical wound, including those at angled parts of the spine. Furthermore, due to the rigidity achieved by the construction of the blade members and connectors, the system provides optimum retraction along the length of the surgical wound with a minimum use of retractor handles or other hardware.

While the present invention has been described in reference to the preferred embodiments of the invention, it is recognized that other embodiments may be made without departing from the present inventive concept. Such other embodiments are considered to be within the scope of the present invention as defined by the claims herein.

What is claimed is:

1. A surgical retractor system comprising a plurality of serially connectable retractor blade members, a plurality of connector elements and operating means engagable with said retractor blade members, wherein each of said retractor blade members comprises a retractor blade body and connector element receiving means, said connector element receiving means comprises elongated sleeves formed as an integral part of said retractor blade members, said sleeves are coextensive with at least a portion of at least one edge of said retractor blade members and have a polygonal cross section, and wherein each of said retractor blade members comprises two of said sleeves positioned along opposite edges of said retractor blade body so as to be parallel and wherein adjacent retractor blade members are abuttable along said sleeves; whereby said retractor blade members are connectable in series by said connector elements thereby forming an auxiliary surgical retractor blade of variable height and length.

2. The surgical retractor system of claim 1 wherein said connector elements comprise pin members having a head part and two legs depending from said head part normal thereto and in a mutually parallel spaced apart relationship, each of said legs having a length corresponding substantially to the length of said sleeves, a polygonal cross section corresponding to the cross section of said sleeves and being receivable therein, said legs being spaced apart a distance corresponding to the space between the adjacent sleeves of abutting retractor blade members.

3. The surgical retractor system of claim 2 further comprising cooperating retention means on said legs and said connector receiving means whereby said connector elements are retained within said sleeves.

4. The surgical retractor system of claim 3 wherein said cooperating retention means comprises cooperating detents on said connector legs and said sleeves.

5. The surgical retractor system of claim 3 wherein said cooperating retention means comprises a friction fit of said connector means within said sleeves.

6. The surgical retractor system of claim 2 wherein abuttable sides of said sleeves are flat.

7. The surgical retractor system of claim 1 wherein said connector elements comprise pin members having a head part and two legs depending from said head part in a spaced apart diverging manner at a fixed angle, each of said legs having a length corresponding substantially to that of said sleeves, a polygonal cross section corresponding to that of said sleeves and being receivable therein whereby said retractor blade members are connectable to form an angular retractor blade.

8. The surgical retractor system of claim 2 wherein said connector elements further comprise two parallel, spaced legs extending from said head part opposite said two legs depending from said head part and in an identical mutually spaced apart relationship, whereby said connector elements have an "H" shape and whereby said legs are receivable in said sleeves of said retractor blade members whereby said retractor blade members are connectable in a vertically and horizontally adjacent series.

9. The surgical retractor system of claim 1 wherein said connector elements comprise pin members having two pairs of oppositely extending legs, said pairs of legs being separated by a cross bar, wherein the legs of each pair are parallel and spaced apart a distance corresponding to the space between the adjacent sleeves of abutting retractor blade members and have a polygonal cross section corresponding to the cross section of said sleeves, whereby said blade members are connectable vertically and horizontally by said pin members by insertion of one pair of legs into abutting sleeves of a first pair of horizontally adjacent blade members and insertion of the other pair of legs into abutting sleeves of a second pair of horizontally adjacent blade members, said first and second pairs of blade members being vertically adjacent.

10. The surgical retractor system of claim 1 further comprising tissue engaging means on one side of said retractor blade members providing non-slip engagement with tissues to be retracted.

11. The surgical retractor system of claim 10 wherein said tissue engaging means comprises teeth integrally formed as part of said retractor blade members.

12. The surgical retractor system of claim 10 wherein said tissue engaging means comprises tooth plates formed separately from said retractor blade members and attached thereto in fixed relationship therewith.

13. The surgical retractor system of claim 5 wherein said operating means comprises a surgical retractor handle.

14. The surgical retractor system of claim 13 further comprising engaging means whereby said operating means is engagable with said blade members.

15. The surgical retractor system of claim 14 wherein said engaging means comprises connector pins receivable in said sleeves and having means thereon to cooperate with a surgical retraction instrument.

* * * * *